US009726470B2

(12) United States Patent
Biber et al.

(10) Patent No.: US 9,726,470 B2
(45) Date of Patent: Aug. 8, 2017

(54) IDENTIFYING A POSITION OF TRANSMISSION/RECEPTION COILS OF A MAGNETIC RESONANCE IMAGING SCANNER WITH LABELS READ IN MOTION

(71) Applicants: Stephan Biber, Erlangen (DE); Gerhard Metz, München (DE)

(72) Inventors: Stephan Biber, Erlangen (DE); Gerhard Metz, München (DE)

(73) Assignee: Siemens Aktiengesellschaft, München (DE)

( * ) Notice: Subject to any disclaimer, the term of this patent is extended or adjusted under 35 U.S.C. 154(b) by 1021 days.

(21) Appl. No.: 13/974,753

(22) Filed: Aug. 23, 2013

(65) Prior Publication Data

US 2014/0055127 A1    Feb. 27, 2014

(30) Foreign Application Priority Data

Aug. 23, 2012   (DE) ........................ 10 2012 215 007

(51) Int. Cl.
*G01B 7/00* (2006.01)
*G01R 33/36* (2006.01)
(Continued)

(52) U.S. Cl.
CPC ............ *G01B 7/003* (2013.01); *A61B 5/0555* (2013.01); *G01R 33/3692* (2013.01); *A61B 2562/08* (2013.01); *G01R 33/341* (2013.01)

(58) Field of Classification Search
CPC  G01R 33/3692; G01R 33/3415; G01R 27/28; G01R 33/341; G01R 33/36;
(Continued)

(56) References Cited

U.S. PATENT DOCUMENTS

2006/0232275 A1* 10/2006 Leussler ............ G01R 33/3692
324/322
2007/0096739 A1*  5/2007 Nakabayashi ..... G01R 33/3415
324/318
(Continued)

FOREIGN PATENT DOCUMENTS

DE           10314215 B4    11/2006
WO       WO2005017548 A1     2/2005

OTHER PUBLICATIONS

German Office Action cited in German Application No. 10 2012 215 007.2, mailed May 23, 2013.

*Primary Examiner* — Melissa Koval
*Assistant Examiner* — Rishi Patel
(74) *Attorney, Agent, or Firm* — Lempia Summerfield Katz LLC (57) ABSTRACT

A method and a device for identifying a position of a local coil of a magnetic resonance imaging scanner relative to a position of a patient couch are provided. The device includes at least one reading unit that is configured to determine a position of at least one label at the local coil relative to the at least one reading unit. The device also includes a position determination apparatus that is configured to determine the position of the patient couch relative to the magnetic resonance imaging scanner. The device includes a position determination apparatus that is configured to determine the position of the local coil relative to the patient couch based on the determined position of the at least one label and the determined position of the patient couch.

46 Claims, 3 Drawing Sheets

(51) Int. Cl.
*A61B 5/055* (2006.01)
*G01R 33/341* (2006.01)

(58) Field of Classification Search
CPC ............ G01R 33/3664; A61B 2562/08; A61B 5/0555; G01B 7/003
See application file for complete search history.

(56) References Cited

U.S. PATENT DOCUMENTS

| | | | |
|---|---|---|---|
| 2010/0052682 A1 | 3/2010 | Mueller | |
| 2014/0055132 A1* | 2/2014 | Biber | ................. G01R 33/3664 324/307 |
| 2014/0055148 A1* | 2/2014 | Biber | ................. G01R 33/3692 324/629 |

* cited by examiner

IDENTIFYING A POSITION OF TRANSMISSION/RECEPTION COILS OF A MAGNETIC RESONANCE IMAGING SCANNER WITH LABELS READ IN MOTION

This application claims the benefit of DE 10 2012 215 007.2, filed on Aug. 23, 2012, which is hereby incorporated by reference.

BACKGROUND

The present embodiments relate to methods and devices for identifying the position of transmission/reception coils of an MRI scanner.

Magnetic resonance imaging (MRI) scanners for examining objects or patients by magnetic resonance imaging are known from, for example, DE10314215B4.

SUMMARY

The scope of the present invention is defined solely by the appended claims and is not affected to any degree by the statements within this summary.

The present embodiments may obviate one or more of the drawbacks or limitations in the related art. For example, identification of a position of transmission/reception coils of a magnetic resonance imaging scanner relative to a patient couch is optimized.

DETAILED DESCRIPTION

Figure 4:
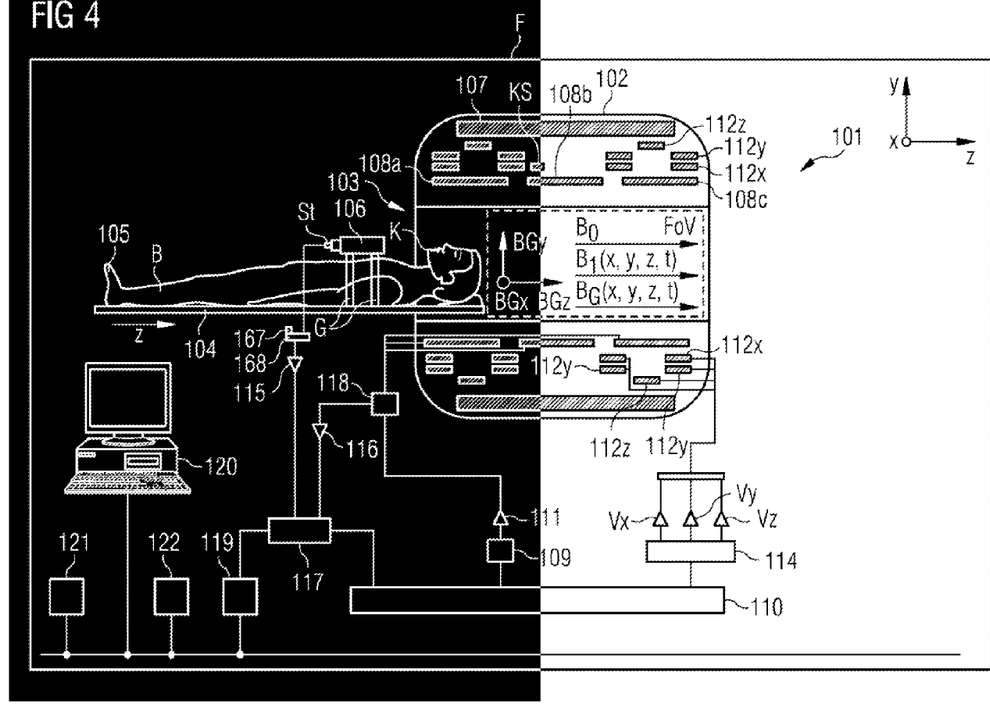
FIG. 4 shows one embodiment of an MRI system.

FIG. 4 shows one embodiment of a magnetic resonance imaging (MRI) scanner 101 (e.g., situated in a shielded room or in a Faraday cage F) with a whole body coil 102 with a space 103 (e.g., tubular), in which a patient couch 104 (e.g., a patient table) with a body of, for example, an examination object 105 (e.g., of a patient; with or without local coil arrangement 106) may be driven in the direction of the arrow z in order to generate images of the patient 105 by an imaging method. Arranged on the patient is, for example, a local coil arrangement 106, by which, in a local region (e.g., a field of view (FOV)) of the MRI scanner, recordings of a portion of the body 105 may be generated. Signals of the local coil arrangement 106 may be evaluated (e.g., converted into images, stored or displayed) by an evaluation apparatus (e.g., including elements 168, 115, 117, 119, 120, 121) of the MRI scanner 101. The evaluation apparatus may be connected to the local coil arrangement 106 by, for example, coaxial cables or by radio (e.g., element 167).

In order to use a magnetic resonance imaging MRI scanner 101 to examine the body 105 (e.g., an examination object or a patient) using magnetic resonance imaging, different magnetic fields are radiated onto the body 105. The magnetic fields are matched very precisely to one another in terms of temporal and spatial characteristics. A strong magnet (e.g., a cryo-magnet 107) in a measuring cabin with an opening 103 (e.g., tunnel-shaped) generates a static strong main magnetic field $B_0$ that may be, for example, 0.2 tesla to 3 tesla or more. The body 105 to be examined, supported by the patient couch 104, is driven into a region of the main magnetic field $B_0$ that is approximately homogeneous in the observation region FoV. The nuclear spins of atomic nuclei of the body 105 are excited by magnetic radiofrequency excitation pulses B1 (x, y, z, t) that are, for example, radiated in by a radiofrequency antenna that is illustrated in a highly simplified fashion as body coil 108 (e.g., a multi-part body coil 108a, 108b, 108c; and/or, optionally, a local coil arrangement). Radiofrequency excitation pulses are generated by, for example, a pulse generation unit 109 that is controlled by a pulse sequence control unit 110. After amplification by a radiofrequency amplifier 111, the pulses are routed to the radiofrequency antenna 108. The radiofrequency system shown is merely indicated schematically. In other embodiments, more than one pulse generation unit 109, more than one radiofrequency amplifier 111 and several radiofrequency antennas 108a, b, c are employed in a magnetic resonance imaging scanner 101.

The magnetic resonance imaging scanner 101 includes gradient coils 112x, 112y, 112z, by which magnetic gradient fields $B_G$ (x, y, z, t) for selective slice excitation and for spatial encoding of the measurement signal are radiated in during a measurement. The gradient coils 112x, 112y, 112z are controlled by a gradient coil control unit 114 (and optionally via amplifiers Vx, Vy, Vz) that, like the pulse generation unit 109, is connected to the pulse sequence control unit 110.

Signals emitted by the excited nuclear spins (of the atomic nuclei in the examination object) are received by the body coil 108 and/or at least one local coil arrangement 106, amplified by associated radiofrequency preamplifiers 116 and processed further and digitized by a reception unit 117. The recorded measurement data is digitized and stored as complex number values in a k-space matrix. An associated MRI image may be reconstructed from the k-space matrix filled with values by a multidimensional Fourier transform.

For a coil that may be operated both in the transmission and in the reception mode, such as, for example, the body coil 108 or a local coil 106, the correct signal transmission is regulated by an upstream transmission/reception switch 118.

An image processing unit 119 generates an image from the measurement data. The image is displayed to a user via an operating console 120 and/or stored in a storage unit 121. A central computer unit 122 controls the individual components of the installation.

In MR imaging, images with a high signal-to-noise ratio (SNR) may be recorded using local coil arrangements (e.g., coils, local coils). The local coil arrangements are antenna systems that are attached in the direct vicinity on (anterior) or under (posterior) or at or in the body 105. During an MR measurement, the excited nuclei induce a voltage in the individual antennas of the local coil. The induced voltage is amplified using a low-noise preamplifier (e.g., LNA, preamp) and relayed to the reception electronics. In order to improve the signal-to-noise ratio, even in the case of high-resolution images, high field installations (e.g., 1.5 T-12 T or more) are used. If it is possible to connect more individual antennas to an MR reception system than there are receivers available, then, for example, a switching matrix (e.g., RCCS) is installed between reception antennas and receiver. The switching matrix routes the currently active reception channels (e.g., the reception channels that currently lie in the field of view of the magnet) to the available receivers. As a result of this, more coil elements than there are receivers available may be connected since, in the case of a whole body coverage, only those coils that are situated in the FoV or in the homogeneity volume of the magnet are to be read out.

By way of example, an antenna system that may, for example, include one antenna element, or as an array coil, a plurality of antenna elements (e.g., coil elements), may be referred to as local coil arrangement 106. These individual antenna elements are, for example, embodied as loop antennas (e.g., loops), butterfly coils, flex coils or saddle coils. By way of example, a local coil arrangement includes coil elements, a preamplifier, further electronics (e.g., sheath current chokes), a housing, supports and may include a cable with plugs by which the coil elements are connected to the MRI scanner. A receiver 168, attached on the installation side, filters and digitizes a signal received from a local coil 106 (e.g., by radio), and transmits the data to a digital signal processing apparatus that may derive an image or spectrum from the data obtained by a measurement and makes the image or spectrum available to the user for, for example, a subsequent diagnosis by the user and/or for storage purposes.

Figure 1:
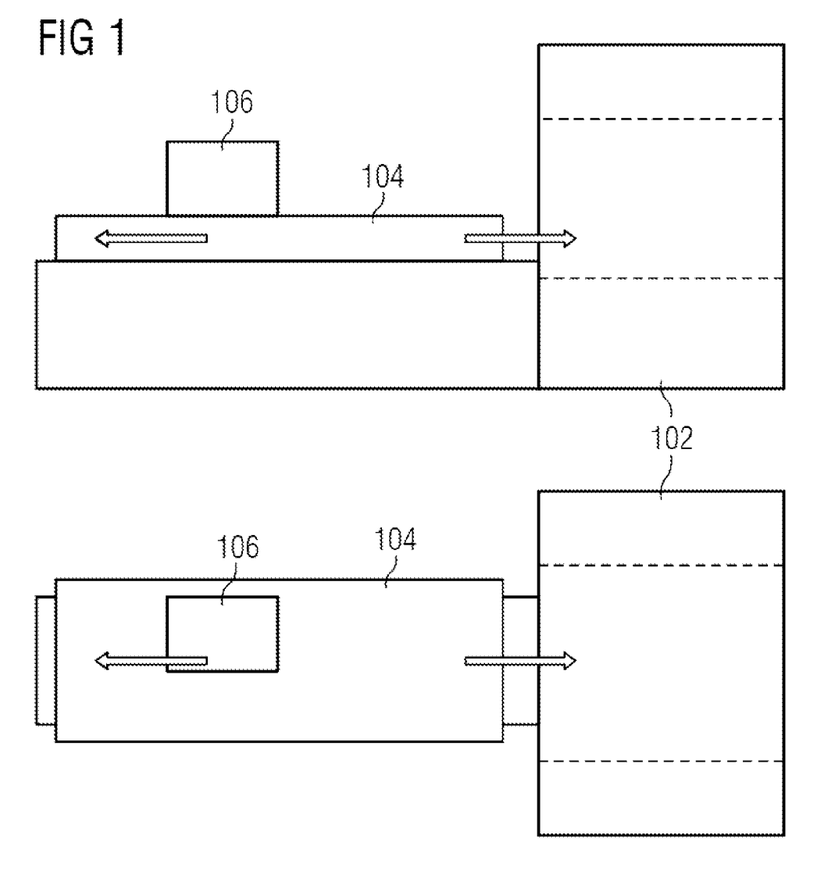
FIG. 1 shows, in a side view at the top of FIG. 1 and in a top view at the bottom of FIG. 1, a local coil as a transmission/reception coil on a patient couch during entry into a bore (e.g., entrance) of a magnetic resonance imaging (MRI) scanner.
Figure 2:
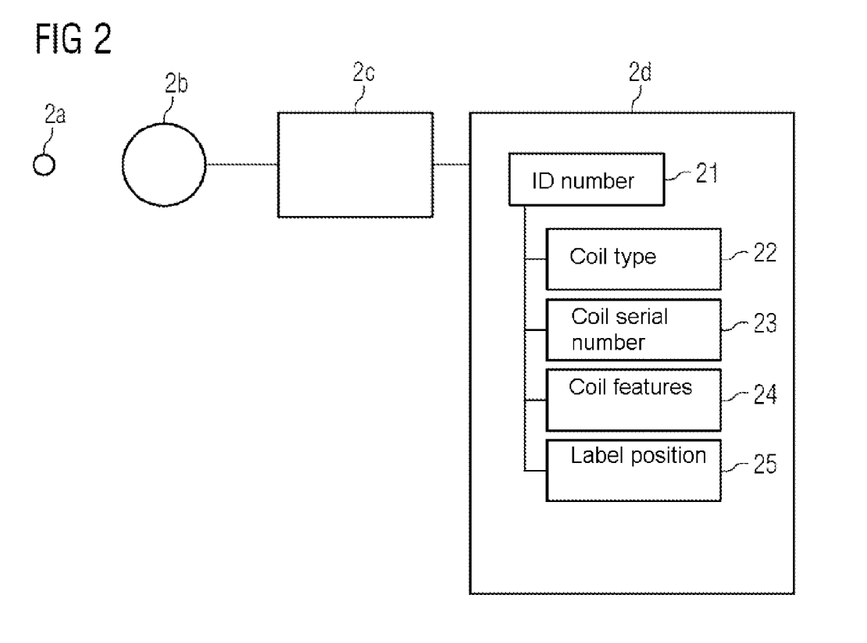
FIG. 2 shows one embodiment including a label, a reading unit and a database with local coil identity number, associated local coil type, local coil serial number, local coil features and determined label position.
Figure 3:
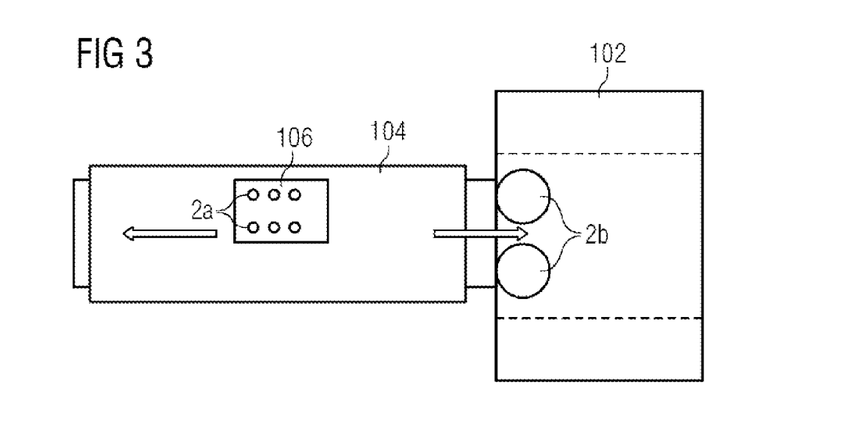
FIG. 3 shows, in a simplifying manner, a top view of one embodiment of an MRI scanner with at least one label on a local coil, reading antennas of a reading unit at a MRI bore entrance, and a position determination apparatus for determining the position of the at least one label relative to the position of the patient couch.

FIGS. 1 to 3 show embodiments of methods and MRI scanners.

In a magnetic resonance tomography (MRI) scanner 101, a patient 105 is transported into and out of the measurement region FoV of an MRI scanner 101, 102 while, for example, lying on a table 104 (e.g., patient table, patient couch). In some measurement methods, local coils 106 are attached to the patient couch 104 in the vicinity of the body tissue to be examined. The local coils serve for receiving and/or transmitting electromagnetic signals. There is a plurality of different types of local coils, and every local coil or local coil arrangement has individual features. The local coils or local coil arrangements may be placed onto the patient couch 104 at different positions and affixed to the patient couch 104. The MRI system 101 should know the position of the employed local coils or local coil arrangements 106 relative to the patient couch 104 sufficiently well to be able to displace the patient couch 104 relative to an MRI scanner housing 101 in a suitable fashion.

In accordance with one embodiment, the position of the local coils 106 or local coil arrangements 106 is determined with the aid of electronically wirelessly readable labels 2a. Each local coil or local coil arrangement 106 is provided with at least one electronically readable label 2a. Each label 2a carries a unique ID number 21 (e.g., identity number) that is only allocated once. Data with respect to the local coil 106 or local coil arrangement 106 (e.g., array) associated with the label 2a, including label position data 25 for the determined position of the label 2a relative to the local coil or local coil arrangement and optional local coil features 24 and/or a local coil serial number 23, are stored in a database 2d. By way of example, how the label position 25 of a label 2a or the positions of several labels 2a on a local coil or local coil arrangement 106 is relative to the local coil or local coil arrangement 106 may be stored (2d) and evaluated using a control 110. For example, the coil type 22 and coil features may be determined for specific local coils on account of the ID number 21 of the labels 2a arranged on the local coil arrangement 106. Additionally, the position of antennas in the local coil arrangement and/or interfaces of the local coil arrangement relative to the labels 2a may also be determined. From this, a computer 110 of the MRI scanner may determine these positions on the local coil and, for example, compare the positions to prescriptions.

The ID numbers of the electronically readable labels 2a may be read out wirelessly by appropriate reading units 2c (e.g., as RFID). In this case, at least one reading unit 2c with at least one reading antenna 2b is attached, for example, to the entrance (e.g., bore 103) of the MRI scanner housing 102 (e.g., MRI measuring tube) or integrated into the MRI scanner housing 102. A local coil 106 or local coil arrangement 106 (e.g., array of local coils) mounted on the patient couch enters into the bore 103 of the MRI scanner housing 102 (e.g., MRI scanner measurement tube) with the patient table 104. As soon as one or more labels 2a of the local coil or local coil arrangement 106 enter into the reading region of one or more reading units 2c or reading antennas 2b of reading units 2c on the MRI scanner housing, the ID numbers 21 of the labels 2a are read. From the time profile of identifying the various labels 2a by the reading units 2c (e.g., entering and leaving the reading region, signal strength of the label signal) while the patient couch slowly enters the MRI scanner housing (e.g., MRI scanner measurement tube), the MRI system is able to draw conclusions about the changing position of the local coil or the local coil arrangement relative to the MRI scanner housing.

Since the MRI system 101, 110 knows the position of the patient couch relative to the MRI scanner housing at all times, the position of the local coil 106 or local coil arrangement 106 may be determined relative to the patient couch by combination.

Since the MRI scanner measurement system should know the position of the local coils or the local coil arrangements on the patient couch, these requirements were previously solved differently (e.g., by mechanical encoding or light visors). Many MRI systems make use of optical measurement systems. An optically identifiable marking is attached to the local coil or local coil arrangement. The local coil or local coil arrangement is mounted on the patient couch at a position that depends on the local coil type, the patient and the body tissue to be examined. An optical measurement apparatus (e.g., light pointer) is situated at the entrance to the MRI scanner housing (e.g., MRI scanner measurement tube). The patient couch with patient and local coil or local coil arrangement is manually inserted into the MRI scanner housing (e.g., MRI scanner measurement tube) until the light signal of the optical measurement apparatus points to the marking on the local coil or local coil arrangement. At this point, the correspondence of the marking with the optical pointer is manually communicated to the MRI system. Since the current position of the patient couch relative to the MRI scanner housing is known to the MRI system, the position of the local coil or local coil arrangement may therefore be calculated relative to the patient couch. This process uses manual intervention by the operating staff and uses a substantial part of the whole examination time.

Mechanical encoding methods are disadvantageous because mechanical encoding methods prescribe a fixed position of the local coil on the patient couch. By way of example, in the case of a knee coil, this may require the patient, after lying on the patient couch, to slide or be moved once again in the longitudinal direction of the table in order to position the knee precisely in the center of the local coil. This may be disadvantageous for the patient workflow. In other words, the restricted spatial flexibility of the local coil positioning involves disadvantages in the workflow that are solved by one or more of the present embodiments.

There are MRI-based methods that employ the spectrum of the received MR signal in order to detect the local coil position in the MRI scanner measurement tube. However, these methods only work in the homogeneity volume and use techniques similar to MRI imaging (e.g., gradients, transmission pulses, evaluation of the RX spectrum).

In accordance with FIG. 1, the patient may lie on the patient couch 104 during an MRI recording. The local coil 106 or local coil arrangement 106 (e.g., array of a plurality of local coils) is attached to the patient couch 104 at the body site to be examined and connected to the MRI system 101, 110 via a cable to an interface on the patient couch (e.g., connected to the MRI system). For the actual MRI recording, the patient couch with patient 105 and local coil 106 is inserted into the MRI scanner housing or "bore" 102 and subsequently removed therefrom again. In contrast to other methods for determining the position of local coils on the patient couch 104 on a magnetic resonance imaging scanner 101, according to one embodiment, the interaction between electronically wirelessly readable labels 2a and the reading units 2c thereof is used in order to establish the position of the local coil or local coils 106.

As shown in FIG. 2, one embodiment of a system with electronically wirelessly readable labels 2a includes at least one reading unit 2c with one or more reading antennas 2b, integrated therein or separated therefrom, and at least one electronically readable label 2a. Stored in each label 2a is at least one identity (ID) number 21 that is only allocated once and may be read wirelessly by the reading unit 2c over a definable distance between reading antenna 2b and label 2a.

Using the read ID number 21 of the label 2a, the MRI system 101 establishes from a database 2d, in addition to other data, the position 25 of the label 2a relative to the local coil 106 or local coil arrangement 106, on which the label 2a is immovably applied (e.g., adhesively bonded or installed).

By way of example, in accordance with FIG. 3, a position determination of the position of the local coil or local coil arrangement 106 relative to the patient couch 104 may be carried out as follows by the MRI system 101.

One or more electronically readable labels 2a are attached to the housing of the local coil or local coil arrangement 106 or integrated into the housing. One or more reading units 2c and/or the associated reading antennas 2b (e.g., of the reading units 2c) are attached on or in the vicinity of, for example, the entrance of the MRI scanner housing 102 (e.g., MRI scanner measurement tube) or a stationary part of the patient couch 104 on the MRI scanner housing 102 or integrated into the MRI scanner housing 102. In the case of a large reading region, the reading system may already identify the local coil or local coil arrangement on the patient couch when the table is still situated outside of the MRI scanner housing (e.g., only a rough position determination is possible). In the case of a small reading region, the local coil or local coil arrangement, which is situated in the vicinity of the patient couch, may also only be identified when the table enters the MRI scanner housing (e.g., MRI scanner measurement tube; more precise position determination is possible). The labels 2a are read dynamically during the entry or exit of the patient couch 104. As a result, even a small set reading region reaches all possible mounting positions of a local coil or local coil arrangement 106 on the patient couch 104. In this case, all reading units 2c record the time profile of, for example, all read labels 2a in detail (e.g., entry into the reading region, profile of the signal strength within the reading region, exit from the reading region). The time position profile of the local coil or local coil arrangement 106 relative to the MRI scanner housing 102, 103 is established with the aid of known methods (e.g., averaging of entry and exit times, signal maxima) from the profile data of all labels 2a and reading units. The MRI system 101, 110 measures the position of the patient couch 104 relative to the MRI scanner housing 102, 103 at all times. In one embodiment, this may be used to establish the position of the local coil or local coil arrangement 106 relative to the patient couch 104 by combination.

Compared to previously employed methods for determining the position of local coils on a magnetic resonance imaging scanner, an advantage that may emerge from employing electronically wirelessly readable labels 2a is that the position determination of MRI systems may take place automatically, without manual intervention such as displacing the patient couch 104 or operating an optical measurement system.

Additionally, the position determination may be carried out in a comparatively short time. The overall time of an MRI recording is reduced, the operating staff and the patients are unburdened and the costs per recording are reduced.

The position is already determined during the entry of the patient couch 104 into the MRI scanner housing 102 (e.g., MRI scanner measurement tube, bore) directly before the imaging MRI recording. If no inadmissible position of the local coil or local coil arrangement 106 was selected, an MRI recording with an entry and exit of the patient couch 104 may be carried out without a pause for an optical position measuring process. As a result of the concentrated reading position at the entrance of the MRI scanner housing, only one, two, three or more reading units 2c or reading antennas 2b are used. If the reading units 2c or reading antennas 2b were to be displaced into the patient couch 104 or into the local coils 106 or local coil arrangements 106, significantly more reading units 2c may be used. Reading units 2c for electronically wirelessly readable labels 2a may be significantly more expensive than the associated labels 2a.

As a result of using the wirelessly/electronically (e.g., by radio or RFID radio) readable labels 2a, together with the data 22-25 stored in a database 2d, the identification of the utilized local coils 106 or local coil arrangement 106 may be achieved without additional complexity by the MRI system 101. As a result, it is, independently of a connection to the system to be established manually (e.g., in which it is possible to forget to plug-in a plug), provided that only types and an approved number of local coils 106 or local coil arrangements 106 that are approved for the utilized measurement mode and properly functioning units are used. If a local coil 106 or local coil arrangement 106 is identified individually (e.g., by comparing the transmitted ID number 21 and/or RFID of the local coil with a table of RFID numbers and associated local coil types in the MRI scanner 101, 110), the MRI system 101, 110 may be set to individual features of the local coil 106 or the local coil arrangement 106. The safety of the patient 105 and the reliability of the measurement system 101, as well as the quality of the MRI scanner measurement results, are increased.

An additional use may include the detection of local coils not plugged into the MRI system 101 that may constitute a potential risk to the patient 105 (e.g., possible vibrating of a local coil 106 by coupling with the body coil and therefore increased SAR values). This identification may also be of assistance in meeting standard requirements. It is advantageous in this embodiment if the reading antennas 2b of the reading units 2c for the electronically readable labels 2a do not lie in the FoV and therefore are not exposed to the high RF transmission power of the MRI system 101 or able to have possible negative feedback to other antennas (e.g., coupling, reduction of the quality, maladjustment).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for identifying a position of a local coil of a magnetic resonance imaging scanner relative to a patient couch with at least one label, the method comprising:
   wirelessly transmitting an identity number by the at least one label, wherein the identity number comprises label position data of the at least one label;
   reading, by at least one reading unit, the identity number of the at least one label;
   determining a position of the at least one label relative to the at least one reading unit;
   determining a position of the patient couch relative to the magnetic resonance imaging scanner;
   determining the position of the at least one label relative to the patient couch from the position of the at least one label relative to the at least one reading unit and from the position of the patient couch relative to the magnetic resonance; and
   establishing, with a magnetic resonance imaging system, at least a position of the at least one label relative to the local coil or a local coil arrangement, on which the label is attached, with the identity number of the at least one label read by the at least one reading unit using a database.

2. The method as claimed in claim 1, wherein the reading of the identity number of the at least one label occurs during a movement of the at least one label, of the local coil, or of the at least one label and the local coil relative to the at least one reading unit.

3. The method as claimed in claim 1, wherein the at least one label or the at least one reading unit is arranged at the magnetic resonance imaging scanner.

4. The method as claimed in claim 3, wherein the at least one label or the at least one reading unit is arranged at a bore or at an entrance to the bore of the magnetic resonance imaging scanner.

5. The method as claimed in claim 1, wherein each label of the at least one label is an RFID label, and
   wherein each reading unit of the at least one reading unit is an RFID reading unit.

6. The method as claimed in claim 1, wherein the at least one reading unit is only one reading unit.

7. The method as claimed in claim 6, wherein determining the position of the at least one label comprises determining, with the one reading unit, the position of a plurality of labels relative to the one reading unit.

8. The method as claimed in claim 1, wherein the at least one reading unit comprises a plurality of reading units, and
   wherein the determining the position of the at least one label comprises determining, with the plurality of reading units, the position of the at least one label relative to the plurality of reading units.

9. The method as claimed in claim 1, wherein determining the position of the patient couch comprises determining the position of the patient couch relative to the magnetic resonance imaging scanner with a motor control, detectors at the patient couch, the at least one label, or a combination thereof.

10. The method as claimed in claim 1, wherein the identity number is only allocated once and is stored in each label of the at least one label.

11. The method as claimed in claim 1, wherein one or more labels of the at least one label are attached to a housing of a local coil arrangement or the local coil, are integrated into the housing of the local coil arrangement or the local coil, or a combination thereof.

12. The method as claimed in claim 1, wherein one or more reading units of the at least one reading unit, reading antennas of the one or more reading units, or a combination thereof are attached to or integrated in a magnetic resonance imaging scanner housing, a measurement tube of the magnetic resonance imaging scanner housing, or a stationary part of the patient couch.

13. The method as claimed in claim 1, wherein the at least one reading unit is configured to identify the position of the at least one label when the patient couch is situated outside of a magnetic resonance imaging bore, when the patient couch enters the magnetic resonance imaging bore, or a combination thereof.

14. The method as claimed in claim 1, wherein the at least one reading unit is configured to read the at least one label during entry, exit, or the entry and the exit of the patient couch.

15. The method as claimed in claim 14, wherein the at least one reading unit is configured to read the at least one label a plurality of times during the entry, the exit, or the entry and the exit of the patient couch.

16. The method as claimed in claim 1, wherein the at least one reading unit, the magnetic resonance imaging scanner, or the at least one reading unit and the magnetic resonance imaging scanner are configured to store data at a plurality of points in time for the at least one read label, the data relating to an entrance into a reading region of the at least one reading unit, a profile of a signal strength within the reading region, an exit from the reading region, or a combination thereof.

17. The method as claimed in claim 1, further comprising establishing a temporal position profile of the at least one label relative to a magnetic resonance imaging scanner housing from data stored at a plurality of points in time by the at least one reading unit for the at least one label.

18. The method as claimed in claim 1, further comprising:
   detecting an identity of each label of a plurality of labels, the plurality of labels comprising the at least one label; and
   storing position data together with the identity of the label for which position data was detected.

19. The method as claimed in claim 1, further comprising detecting when the local coil positioned on the patient couch is not plugged into a magnetic resonance imaging system.

20. The method as claimed in claim 19, wherein the detecting comprises comparing each plugged-in local coil detected at an interface on the patient couch with local coils detected based on the identity number received from the at least one label.

21. The method as claimed in claim 1, wherein determining the position of the at least one label comprises determining with reading antennas of the at least one reading unit are situated outside of a field of view of the magnetic resonance imaging scanner.

22. The method as claimed in claim 1, wherein the position of the at least one label is determined at the at least one reading unit as a function of a measure by the at least one reading unit and stored data relating to the position of the at least one label.

23. A device for identifying a position of a local coil of a magnetic resonance imaging scanner relative to a position of a patient couch, the device comprising:
at least one reading unit configured to:
receive a wirelessly transmitted identity number from at least one label, wherein the identity number comprises label position data of the at least one label;
read the transmitted identity number of the at least one label;
determine a position of the at least one label at the local coil relative to the at least one reading unit; and
establish at least a position of the at least one label relative to the local coil or a local coil arrangement, on which the label is attached, with the identity number of the at least one label read by the at least one reading unit using a database; and
a position determination apparatus configured to:
determine the position of the patient couch relative to the magnetic resonance imaging scanner; and
determine the position of the local coil relative to the patient couch based on the determined position of the at least one label and the determined position of the patient couch.

24. The device as claimed in claim 23, wherein the at least one label is arranged on the local coil, and
wherein the at least one reading unit is configured to receive the identity number by radio.

25. The device as claimed in claim 23, wherein the at least one label or the at least one reading unit is arranged on the magnetic resonance imaging scanner.

26. The device as claimed in claim 25, wherein the at least one label or the at least one reading unit is arranged on the magnetic resonance imaging scanner at a bore or at an entrance to the bore of the magnetic resonance imaging scanner.

27. The device as claimed in claim 23, wherein the identity number received by the at least one reading unit is wirelessly readable.

28. The device as claimed in claim 23, wherein each label of the at least one label is an RFID label, and
wherein each reading unit of the at least one reading unit is an RFID reading unit.

29. The device as claimed in claim 23, wherein the at least one reading unit is only one reading unit.

30. The device as claimed in claim 23, wherein the at least one label comprises a plurality of labels, and
wherein positions of the plurality of labels relative to the at least one reading unit are determined with the at least one reading unit.

31. The device as claimed in claim 23, wherein the at least one reading unit comprises a plurality of reading units, and
wherein the position of the at least one label relative to the plurality of reading units is determined with the plurality of reading units.

32. The device as claimed in claim 23, wherein the position of the patient couch relative to the magnetic resonance imaging scanner is determined with the aid of a motor control, detectors at the patient couch, or a combination thereof.

33. The device as claimed in claim 23, wherein the identity number received by the at least one reading unit is only allocated once.

34. The device as claimed in claim 23, wherein the device is configured to enable at least a position of the at least one label relative to the local coil or a local coil arrangement, on which the label is attached, to be established by a magnetic resonance imaging (MRI) system with aid of the identity number of the at least one label read by the at least one reading unit using a database.

35. The device as claimed in claim 23, wherein one or more labels are attached to a housing of a local coil arrangement or a local coil, integrated into the housing of the local coil, or a combination thereof.

36. The device as claimed in claim 23, wherein one or more reading units, reading antennas of the one or more reading units, or the one or more reading units and the reading antennas of the one or more reading units are attached to or integrated in a magnetic resonance imaging scanner housing or a measurement tube of the magnetic resonance imaging scanner housing, or on a stationary part of the patient couch.

37. The device as claimed in claim 23, wherein the at least one reading unit is configured to enable the position of the at least one label to be identified when the patient couch is situated outside of a magnetic resonance imaging bore, when the patient couch enters the magnetic resonance imaging bore, or when the patient couch is situated outside of the magnetic resonance imaging bore and when the patient couch enters the magnetic resonance imaging bore.

38. The device as claimed in claim 23, wherein the at least one reading unit is configured to enable the at least one label to be read during entry, exit, or the entry and the exit of the patient couch.

39. The device as claimed in claim 38, wherein the at least one reading unit is configured to enable the at least one label to be read a plurality of times during the entry, the exit, or the entry and the exit of the patient couch.

40. The device as claimed in claim 23, wherein the at least one reading unit, the magnetic resonance imaging scanner, or the at least one reading unit and the magnetic resonance imaging scanner are configured such that data is stored at several points in time for the at least one label, the data relating to an entrance into a reading region of the at least one reading unit, a profile of a signal strength within the reading region, an exit from the reading region, or a combination thereof.

41. The device as claimed in claim 23, wherein the device is configured to enable a temporal position profile of the at least one label relative to a magnetic resonance imaging scanner housing to be established from data stored at several points in time by the at least one reading unit for the at least one label.

42. The device as claimed in claim 23, wherein the device is configured to enable an identity of a plurality of labels to be detected and position data to be stored together with the identity of the label for which position data was detected.

43. The device as claimed in claim 23, wherein the device is configured to detect when the local coil is not plugged into a magnetic resonance imaging system.

44. The device as claimed in claim 43, wherein the detection comprises a comparison of each plugged-in local coil detected at an interface on the patient couch with local coils detected based on ID numbers received from labels.

45. The device as claimed in claim 23, wherein reading antennas of the at least one reading unit are situated outside of a field of view of the magnetic resonance scanner.

46. The device as claimed in claim 23, wherein the at least one reading unit is configured to determine the position of the at least one label from stored data relating to the position of at least one label.

\* \* \* \* \*